United States Patent [19]

Reitmeier et al.

[11] Patent Number: 5,663,400
[45] Date of Patent: Sep. 2, 1997

[54] PROCESS FOR PREPARING ALKYLSILANES HAVING BULKY ALKYL RADICALS

[75] Inventors: Rudolf Reitmeier; Hermann Bräunling, both of Burghausen; Tassilo Lindner, Mehring; Hartmut Menzel, Burghausen, all of Germany

[73] Assignee: Wacker-Chemie GmbH, Munich, Germany

[21] Appl. No.: 611,737

[22] Filed: Mar. 6, 1996

[30] Foreign Application Priority Data

Mar. 9, 1995 [DE] Germany ............... 195 08 459.4

[51] Int. Cl.$^6$ ............... C07F 7/08; C07F 7/10
[52] U.S. Cl. ............... 556/479; 556/415
[58] Field of Search ............... 556/479, 415

[56] References Cited

U.S. PATENT DOCUMENTS

| | | | |
|---|---|---|---|
| 3,798,252 | 3/1974 | Nitzsche et al. | 556/479 |
| 5,424,470 | 6/1995 | Bank et al. | |

FOREIGN PATENT DOCUMENTS

| | | |
|---|---|---|
| 0596646 | 5/1994 | European Pat. Off. |
| 0602922 | 6/1994 | European Pat. Off. |
| 602922 | 6/1994 | European Pat. Off. |

*Primary Examiner*—Paul F. Shaver
*Attorney, Agent, or Firm*—Martin Connaughton

[57] ABSTRACT

Di- and trialkylsilanes of the formula $$R_a R^1 R^2_b SiX_c \qquad (I),$$

which comprises reacting mono- and dialkylsilanes of the formula $$R^1 R^2_b SiH_a X_c \qquad (II),$$

with alkenes A having at least 4 carbon atoms, which alkenes are unsubstituted or substituted by fluorine, chlorine or bromine atoms or cyano groups, in the presence of a transition metal catalyst and a hydrocarbon as activator, which hydrocarbon has at least one functional group selected from among aldehyde, keto and epoxy groups or halogen atoms, where in the above formulae (I) and (II), R is a branched or cyclic hydrocarbon radical having at least 4 carbon atoms, which radical is unsubstituted or substituted by fluorine, chlorine or bromine atoms or cyano groups, $R^1$ is an alkyl radical having at least 2 carbon atoms, which radical is unsubstituted or substituted by fluorine, chlorine or bromine atoms or cyano groups, $R^2$ is a hydrocarbon radical having at least 2 carbon atoms, which radical is unsubstituted or substituted by fluorine, chlorine, or bromine atoms or cyano groups, X is a fluorine, chlorine or bromine atom or an alkoxy radical having from 1 to 18 carbon atoms, which radical is unsubstituted or substituted by fluorine, chlorine or bromine atoms or cyano groups, a is 1 or 2, b is 0 or 1 and c is 1 or 2.

8 Claims, No Drawings

PROCESS FOR PREPARING ALKYLSILANES HAVING BULKY ALKYL RADICALS

BACKGROUND OF THE INVENTION

The present invention relates to a process for preparing di- and trialkylsilanes having bulky allyl radicals by hydrosilylation of alkenes with hydrogen-containing silanes in the presence of a transition metal catalyst and an activator.

Dialkyldialkoxysilanes having bulky alkyl radicals on the silicon are now sought by virtually all relatively large polypropylene manufacturers for their Ziegler catalysts of the latest generation. Particularly sought after are silanes having short-chain branched alkyl or cycloalkyl groups. Until recently, these silanes were industrially produced exclusively from chlorosilanes or alkoxysilanes by the expensive organometallic route, i.e., using large amounts of metals such as sodium or magnesium and also solvents, with corresponding large amounts of metal-containing by-products having to be disposed of.

Alkyl- or dialkylsilanes in which at least one of the alkyl radicals has at least 2 carbon atoms and which contain chlorine atoms or alkoxy radicals in addition to hydrogen bonded directly to silicon add, in the presence of noble metal catalysts, in a satisfactory manner only to linear alkenes having a terminal double bond, so-called α-olefins. Thus, the hydrosilylation of branched or cyclic alkenes having at least 4 carbon atoms with silanes such as dichlorosilane having 2 hydrogen atoms bonded directly to silicon leads only to a monoalkylchlorosilane, even if the alkene is present in excess.

EP-A-602 922 describes a process for reacting both hydrogen atoms of chlorine- or alkoxy-containing silanes having 2 hydrogen atoms bonded directly to silicon with cyclic alkenes having at least 4 carbon atoms in the presence of oxygen. However, the passing in of oxygen as described is complicated and dangerous since the hydrogen-containing silanes, which are readily combustible can form ignitable mixtures with oxygen and the further reaction components.

SUMMARY OF THE INVENTION

It is an object of the present invention to provide a simple safe process for preparing di- and trialkylsilanes where at least one alkyl radical is branched or cyclic and has at least 4 carbon atoms and the silanes also contain chlorine atoms or alkoxy radicals.

The present invention relates to a process for preparing di- and trialkylsilanes of the formula

$$R_a R^1{}_b R^2{}_b SiX_c \qquad (I),$$

which comprises reacting mono- and dialkylsilanes of the formula

$$R^1 R^2{}_b SiH_a X_c \qquad (II),$$

with alkenes A having at least 4 carbon atoms, which alkenes are unsubstituted or substituted by fluorine, chlorine or bromine atoms or cyano groups, in the presence of a transition metal catalyst and a hydrocarbon as activator, which hydrocarbon has at least one functional group selected from among aldehyde, keto and epoxy groups or halogen atoms, where in the above formulae (I) and (II), R is a branched or cyclic hydrocarbon radical having at least 4 carbon atoms, which radical is unsubstituted or substituted by fluorine, chlorine or bromine atoms or cyano groups, $R^1$ is an alkyl radical having at least 2 carbon atoms, which radical is unsubstituted or substituted by fluorine, chlorine or bromine atoms or cyano groups, $R^2$ is a hydrocarbon radical having at least 2 carbon atoms, which radical is unsubstituted or substituted by fluorine, chlorine, or bromine atoms or cyano groups, X is a fluorine, chlorine or bromine atom or an alkoxy radical having from 1 to 18 car atoms, which radical is unsubstituted or substituted by fluorine, chlorine or bromine atoms or cyano groups, a is 1 or 2, b is 0 or 1 and c is 1 or 2.

In above formulae (I) and (II) the sum of a, b and c is 3.

The above reaction is particularly important for the addition of alkenes A which are sterically demanding, namely branched or cyclic. However, even linear alkenes having 5 or more carbon atoms are not easily added without an activator. In particular, alkenes having from 4 to 18 carbon atoms are easily added according to the present invention. The alkenes A can have one or more unsaturated C=C bonds in the molecule.

Examples of sterically demanding alkenes A are cyclopentene, cyclohexene, cyclobutene, cyclooctene, cyclopentadiene, norbornene (bicycloheptene), cyclooctadiene, cyclohexadiene, 3-methylcyclopentene, 3-methylcyclopentadiene, isobutene, 2,3-dimethyl-1-butene, 2,4,4-trimethyl-1-pentene (diisobutylene) or 4-methylene-2,2,6,6-tetramethylheptane (triisobutylene).

The radical R is formed by addition of the alkene A to the Si—H group in the silane of formula (II).

The radical $R^1$ preferably has from 2 to 18 carbon atoms. Preferred examples of alkyl radicals $R^1$ are the ethyl, n-propyl, iso-propyl, n-butyl, iso-butyl, sec-butyl, tert-butyl, n-pentyl, iso-pentyl, neo-pentyl, tert-pentyl radicals; hexyl radicals such as the n-hexyl, 2,3-dimethylbutyl, 3,3-dimethylbutyl radicals; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical, dodecyl radicals such as the n-dodecyl radical; octadecyl radicals such as the n-octadecyl radical; cycloalkyl radicals such as the cyclopentyl, cyclohexyl, cycloheptyl, cyclooctyl, norbornyl radicals and methylcyclohexyl radicals. Preferred examples of alkenyl radicals $R^1$ are the linear alkenyl radicals such as the vinyl and the alkyl radical; cyclic alkenyl radicals such as the cyclopentenyl, cyclohexenyl and cyclooctenyl radicals.

Examples of substituted radicals $R^1$ are cyanoalkyl radicals such as the β-cyanoethyl radical and halogenated alkyl radicals such as the 3,3,3-trifluoro-n-propyl radical, the 2,2,2,2',2',2'-hexafluoroisopropyl radical and the heptafluoroisopropyl radical.

The radical $R^2$ preferably has from 2 to 18 carbon atoms. Preferred examples of hydrocarbon radicals $R^2$ are the alkyl and alkenyl radicals specified for $R^1$, and also aryl radicals such as the phenyl, naphthyl, anthryl and phenanthryl radicals; alkaryl radicals such as o-, m-, p-tolyl radicals, xylyl radicals and ethylphenyl radicals; and aralkyl radicals such as the benzyl radical, the α- and the β-phenylethyl radical.

Preferred examples of substituted radical $R^2$ are the substituted alkyl and alkenyl radicals specified for $R^1$, and also haloaryl radicals such as the o-, m- and p-chlorophenyl radical.

If X, is a halogen atom, preference is given to the chlorine atom. If X is an alkoxy radical, preference is given to an alkoxy radical having from 1 to 6 carbon atoms, which radicals are unsubstituted or substituted by fluorine, chlorine or bromine atoms or cyano groups, such as the methoxy, ethoxy, n-propoxy, iso-propoxy, n-butoxy, iso-butoxy, sec-butoxy, tert-butoxy radials, pentyloxy radicals such as the n-pentyloxy radical and hexyloxy radicals such as the n-hexyloxy radical. The methoxy and ethoxy radicals are more preferred. Preference is given to the unsubstituted alkoxy radicals.

Preferred activators have at most 18, in particular 10, carbon atoms. Examples of aldehydes are acetaldehyde, propionaldehyde, n-butyraldehyde and benzaldehyde.

Preferred examples of ketones are acetone, methyl ethyl ketone, diethyl ketone, methyl isopropyl ketone, methyl butyl ketone, acetylacetone, ethyl butyl ketone, cyclopentanone and cyclohexanone. Particular preference is given to methyl-substituted ketones such as acetone and acetylacetone and cyclic ketones such as cyclopentanone and cyclohexanone.

Preferred examples of epoxy compounds are the oxides of propene, butene, cyclopentene and cyclohexene.

Among the halogenated hydrocarbons, particularly in the addition of chlorosilanes, preference is given to chlorinated hydrocarbons. Preferred examples are $CCl_4$, $CHCl_3$, $CH_2Cl_2$, $CH_3Cl$, ethyl chloride, n-propyl chloride, isopropyl chloride, sec-butyl chloride, isobutyl chloride, tert-butyl chloride, 1,1,2-trimethyl-1-propyl chloride, tert-hexyl chloride cyclopentyl chloride, cyclohexyl chloride, alkyl chloride methalkyl chloride and benzyl chloride.

Apart from acetone, secondary and tertiary chlorinated hydrocarbons, preference is given to isopropyl chloride, cyclopentyl chloride and tert-butyl chloride.

The amount of activators used is preferably 0.1% to 10% by weight, in particular 0.3% to 5% by weight, of the total mixture.

Transition metal catalysts which can be used are the customary hydrosilylation catalysts. The elements and compounds of rhodium and, in particular, platinum are suitable. Preferred rhodium complexes are $RhCl_3/PPh_3$ excess, $ClRh(PPh_3)_3$ (Wilkinson catalyst) and $HRh(CO)(PPh_3)_2$.

The platinum catalysts are, for example, solutions of hexachloroplatinic acid or $H_2PtCl_6 \cdot 6\ H_2O$ in alcohols such as isopropanol (Speier catalyst), olefin complexes such as the Karstedt catalyst $(Pt(ViMe_2SiOSiMe_2Vi)_3)$ or phosphine complexes such as $Cl_2Pt(PPh_3)_2$ Platinum can also be deposited on solid support materials such as activated carbon, aluminum oxide or silica gel. The preferred hydrosilylation catalyst is hexachloroplatinic acid/isopropanol or dilutions thereof, for example in cyclopentene or in inert solvents such as hydrocarbons.

Transition metal catalysts are preferably used in a concentration of $10^{-6}$–$10^{-2}$ mole, in particular $10^{-5}$–$10^{-3}$ mole, of catalyst per mole of silane of formula (I) or, expressed in converted form, 2 to 300 mg of platinum per mole of silane of formula (I). For economic reasons, an amount of catalyst of 10–100 mg of Pt/mole of silane is more preferred. Depending on the temperatures used, a considerable amount can be reused by recycling the soluble platinum after removal of the volatile products, e.g., by short-path distillation.

The reaction temperature can be varied within a very wide range. The optimum depends primarily on the reactants, in particular on the alkene A, and the catalyst concentration. With appropriate activation, e.g., using acetone, the reaction can start and proceed to completion even at room temperature. The temperature is preferably from 30° to 190° C., in particular from 70° to 150° C., to avoid the danger of accumulation of reaction energy and the decomposition of the catalyst or reaching the ignition point of the reaction mixture.

Preferably, more than 1 mole of alkene A per mole of the mono- and dialkylsilanes of formula (II) is used. A small excess of alkene A of at least 2%, in particular 1.05–1.5 mole, preferably 1.1–1.3 mole, per mole of silane of formula (II) is preferred.

Since the overall reaction is strongly exothermic, it is advisable in batch operation to continuously meter in at least one component during the reaction and thus keep the internal temperature almost constant.

To prepare the mono- and dialkylsilanes of formula (II), preference is given to reaction silanes of the formula $$R^2{}_bSiH_dX_c \qquad (III),$$

with alkenes B having at least 2 carbon atoms, which alkenes are unsubstituted or substituted by fluorine, chlorine or bromine atoms or cyano groups, in the presence of a transition metal catalyst, where d is 2 or 3 and $R^2$, X, b and c are as defined above.

In a preferred embodiment, the mono- and dialkylsilanes of formula (II) are prepared in the same reactor in which the process or the present invention for preparing di- and trialkylsilanes of formula (I) is carried out (single-vessel reaction). The mono- and dialkylsilanes of formula (II) are preferably not isolated but reacted directly with the alkene A.

However, the silanes of formula (II) can also be prepared by organometallic alkylation of chloro- or alkoxysilanes of the formula $$X_{c+1}SiH_d$$

or by hydride transfer to alkylsilanes of the formula $$R^2{}_bSiX_{c+1},$$

where $R_2$, X, b, c and d are as defined above.

In a single-vessel reaction for preparing the di- and trialkylsilanes of formula (I), silane of formula (III) can be continuously metered into, preferably over a period of from 15 to 60 minutes, the initially charged, approximately equimolar amount of alkene A which already contains the major part of the transition metal catalyst in dissolved form.

However, the procedure can also be reversed and alkene A, or alkene B and then alkene A can be metered into the initially charged silane of formula (III). After addition of activator and a short activation phase, the significantly slower addition reaction of alkene A according to the present invention is carried out. The preparation of the di- and trialkylsilanes of formula (I) can, e.g., in the case of stirred pressure reactors, in turn be readily controlled by means of the internal temperature or the heat balance or simply by means of the respective internal pressure. The pressure measured in the gas phase above the reaction solution here corresponds essentially to the sum of the temperature-dependent partial pressures of the unreacted starting materials. In the case of reactive activators such as methyl ketone or epoxides, which have correspondingly short half-lives, it can be advantageous to meter them in portions and, in part, only during the preparation of the di- and trialkylsilanes of formula (I).

The metering of at least one of the reaction components in an amount corresponding to its consumption enables, by means of a pressure indicator, the process to be readily controlled and both emissions and, in particular, dangerous operating conditions to be avoided from the start. The targeted addition of activators shortens the induction phase of the preparation of the di- and trialkylsilanes of formula (I) and leads to an overall significant increase in the space-time yield. Since the overall reaction is strongly exothermic, in batch operation at least one component is preferably metered in continuously during the reaction and the internal temperature is kept almost constant. This also makes possible fully continuous addition processes having relatively short residence times of less than 30 minutes, which are particularly safe and economical.

Batch processes are preferably carried out in autoclaves. Continuous processes are carried out by separate metering of the starting materials into, for example, a tube or loop reactor which can be thermostated by means of a heat transfer oil. At the end of the continuous reactor, the almost completely reacted mixture is conducted, via a discharge or pressure-retention valve and collected in a steel tank.

Solvents are not necessary for preparing the di- and trialkylsilanes of formula (I), but may be present. Particularly in the case of a metering-controlled reaction procedure, dilution by inert solvents as is recommended in comparable hydrosilylations for safety reasons, e.g., for removal of heat, can be omitted. Small additions of polar solvents such as THF or glycol ethers can be advantageous in the metering of the platinum catalyst into very nonpolar media.

In the following examples, unless otherwise indicated,
a) all amounts are by weight;
b) all pressures are 0.10 MPa (abs.);
c) all temperatures are 20° C.

EXAMPLES

The platinic acid concentrate used for preparation of the catalyst was a 5% strength solution of $H_2PtCl_6 \cdot 6 H_2O$ in isopropanol containing 2% by weight of platinum.
Analysis:
The progress of the reaction was followed by means of GC. GC samples taken were stored on dry ice to avoid subsequent reactions.

I. Batch Operation:

The investigations detailed below by way of example were carried out in a 1 liter stirred steel vessel having a double wall (for thermostating by means of circulated oil) and outlet from Büchi (laboratory stirred autoclave BEP 280 model IV) or in a corresponding 250 l pilot plant. These pressure vessels were each cleaned with acetone, evacuated and flushed free of air using pure nitrogen and thus made inert. Metering into these (low-)pressure stirred vessels fitted with measurement points for internal temperature and pressure was in each case by means of immersed tubes, i.e., into the initially charged and stirred liquid phase.

Examples 1–7

Preparation of dicyclopentyldichlorosilane by reaction of cyclopentene with dichlorosilane Example 1

A 1 liter stirred autoclave is first charged with 236 g (3.4 mole) of cyclopentene together with 5 g of platinic acid/isopropanol solution while stirring and the contents are heated to about 70° C. At this temperature the metering of a total of 305 g (3 mole) of dichlorosilane is commenced, with the first 30 g being added relatively quickly. After the reaction starts, the thermostat temperature is lowered, so that the remainder of $H_2SiCl_2$ can be metered at an internal temperature of about 75° C. and an internal pressure of 6, at most 9, bar over a period of 30 minutes. After a similarly long period of further stirring at 80° C., the dichlorosilane is virtually completely reacted and the pressure is constant. GC analysis at this point shows 78.5% of cyclopentyldichlorosilane (=$CpSiHCl_2$), 4.3% of cyclopentylchlorosilane (=$CpSiH_2Cl$), 0.8% of cyclopentyltrichlorosilane (=$CpSiCl_3$) and 6.3% of excess cyclopentene, as well as a few peaks <1%, particularly at relatively low retention times.

The reaction mixture is activated by addition of 11 g of acetone and heating to 140° C. The end point of this activation phase is indicated by a falling of the pressure or by the commencement of warming as a result of the addition of the remaining cycloolefins. GC no longer shows any $CpSiH_2Cl$, but up to 3.5% of dicyclopentyldichlorosilane (=$Cp_2SiCl_2$, in addition to 1.5% of $Cp_2SiHCl$, 74.1% of $CpSiHCl_2$ and 1.6% of $CpSiCl_3$).

After this activation, the 2nd stage can be carried out in a controlled manner by metering 201 g of cyclopentene into the stirred reactor kept at about 140° C. The metering-rate and thus the heat of reaction are controlled, as in the 1st stage, via the gauge pressure. At pressures <10 bar, barely 1 hour is necessary. When the activity falls or the catalyst has been thermally stressed for a prolonged period, a further 1% of acetone is added. After a period of further stirring for an hour, during which the gauge pressure gradually drops to 3 bar/140° C., the reaction is complete. After cooling to room temperature, the mixture shows no residual pressure. GC analysis of the 754 g of crude product discharged via the bottom valve shows 83.5% of dicyclopentyldichlorosilane and 1.9% of dicyclopentylmonochlorosilane. The crude product contains only 1.2% of the mono-intermediate $CpSiHCl_2$ in addition to 1.8% of $CpSiCl_3$, 1.9% of $SiCl_4$ and 3.2% of cyclopentene (excess), and also a few relatively low-boiling by-products (in each case <1 area-%).

Example 2

As in Example 1, 235 g of cyclopentene are initially charged in a 1 liter stirred reactor and admixed with 4 g of an isopropanol catalyst solution. The metering of a total of 314 g (3 mole) of dichlorosilane containing 3% of cyclopentyl chloride is then commenced at room temperature. After about 1/5 of the "activated" mixture has been pumped relatively quickly into the vigorously stirred initial charge, the charge is heated to 130° C. and the remaining 4/5 of $H_2SiCl_2$ is added over a period of 40 minutes in such a way that this internal temperature remains constant to ±5° and the gauge pressure remains <10 bar. In the further stirring phase at 130°–140° C., a distinct pressure drop to <4 bar which commences within the 1 hour indicates not only the end of the monostage, but the commencement of the 2nd stage. GC analysis at this point shows 83.5% of $CpSiHCl_2$, as well as 3.1% of cyclopentene, 0.9% of $CpSiCl_3$, 3.1% of $Cp_2SiHCl$ and 5.3% of $Cp_2SiCl_2$, but no longer any $CpSiH_2Cl$.

The 2nd stage is immediately carried out again by controlled metering of 198 g of cyclopentene over a period of 1 hour at 130°–140° C. and further stirring at 140°–150° C. For the subsequent alkoxylation, 740 g of a 86% pure dicyclopentyldichlorosilane are taken off at this point According to GC, it additionally contains 2.5% of $Cp2SiHCl$, 1.9% of $CpSiCl_3$, 1.3% of remaining $CpSiHCl_2$ and 2.3% of cyclopentene as the major secondary constituents.

Example 3

3.3 mole (230 g) of cyclopentene +6 g of catalyst solution are initially charged as in Example 1 at 70° C. with intensive mixing and the metering in of dichlorosilane is commenced relatively quickly. After addition of about 100 g of $H_2SiCl_2$ over a period of 10 minutes at 80° C., 5 g of tert-butyl chloride are added. The reaction mixture is heated over a period of 30 minutes to 130° C. and, over the same period of time, the remainder of a total of 304 g (3 mole) of $H_2SiCl_2$ is metered into the activated initial charge thermostated to this temperature. After stirring for an additional 20 minutes at 130°–140° C., the monostage is complete (81.6% of $CpSiHCl_2$; only 2.7% of cyclopentene, 0.6% of $CpSiCl_3$ and 2.1% of $SiCl_4$; plus 4.5% of $Cp_2SiCl_2$ and 2.3% of $Cp_2SiHCl$) and the internal pressure in the reactor has dropped to 6 bar.

A total of 204 g (2.9 mole, 97% pure) of cyclopentene admixed with 1% of tertbutyl chloride are then metered in over a period of about 40 minutes in such a way that the reaction temperature remains at 130°–140° C. After further stirring for about the same time, the gauge pressure in the reactor has dropped to 3 bar. Stirring is continued until room temperature is reached and 732 g of crude dicyclopentyldichlorosilane (83.7% pure according to GC; additionally contains 2.8% of $Cp_2SiHCl$, 2.6% of $CpSiCl_3$, 3.2% of $SiCl_4$ and 2.6% of remaining cyclopentene) can be taken off without problems.

Example 4

Initial charging of dichlorosilane, metering in of cyclopentene

The stirred autoclave is charged with 7 g of Pt/isopropanol solution (=140 mg of Pt) and 15 g of cyclopentene and is dosed. 253 g (2.5 mole) of dichlorosilane are first injected into the autoclave and heated while stirring to 70° C./7 bar. Only 184 g (2.6 mole) of cyclopentene containing 2% of cyclopentyl chloride are then metered in over a period of 40 minutes and the mixture is stirred further for the same length of time at 70°–80° C. During this time, the internal pressure falls gradually from 9 bar to below 3 bar. According to GC, cyclopentene has been largely reacted. 7.1% of cyclopentylmonochlorosilane $CpSiH_2Cl$, 78.9% of $CpSiHCl_2$ and some low boilers have been formed. The dihydrogensilanes and the catalyst inhibition for the 2nd stage are completely degraded in about 2 hours by further stirring of the mixture at from 80° to 140° C.

Controlled metering in of a further 180 g (2.6 mole) of cyclopentene over a period of 1 hour at 140°±5° C. and 2 hours of further reaction gives an approximately 71% pure dicyclopentyldichlorosilane. According to GC, it additionally contains 6.2% of unreacted monostage, i.e., $CpSiHCl_2$, and 5.3% of cyclopentene, besides 2.1% of $Cp_2SiHCl$, 4.6% of $CpSiCl_3$ and 3.5% of $SiCl_4$, as well as some smaller peaks which have not been assigned.

Example 5

Pilot plant

A 250 liter stirred pressure reactor fitted with a safety valve (set to 20 bar) is charged with 58 kg (827 mole) of cyclopentene and 0.5 kg of platinic acid/isopropanol solution while stirring (130 rpm). Commencing at room temperature, a total of 75 kg (740 mole) of $H_2SiCl_2$ are metered into the pressure vessel over a period of barely 1 hour. The first 15 kg are metered in quickly and the mixture is only then heated to 70° C. The remainder of the dichlorosilane is added with gentle cooling (cooling coil in the stirred reactor) so that an internal temperature of 70°–80° C. is established. Subsequently, a further 0.5 kg of catalyst solution diluted with 2 kg of isopropyl chloride (=2-chloropropane) is metered into the mixture over approximately the same period of time, with the reaction temperature being gradually creased to 140° C. The pressure drop in the reactor to below 4 bar/140° C. which can be clearly observed at the end indicates the substantial conversion of cyclopentene and finally the commencement of the 2nd stage (cf. Example 1).

Over the next hour, a further 54 kg of cyclopentene mixed with 1 kg of isopropyl chloride are metered in at 140°–150° C./max. 12 bar. With further stirring for an additional 2 hours, the gauge pressure gradually drops back to values <3 bar/140° C. After stirring until room temperature and atmospheric pressure are reached, the mixture is finally discharged via the bottom valve into metal drums. This gives 188 kg of crude product containing 80.3% of dicyclopentyldichlorosilane. According to GC, it additionally contains 2.1% of $Cp_2SiHCl$, 2.7% of $CpSiCl_3$, 2.8% of remaining $CpSiHCl_2$, 5.1% of cyclopentene and 3.2% of $SiCl_4$ as major secondary constituents.

Example 6

Pilot plant

As in Example 5, 58 kg of cyclopentene +0.7 kg of catalyst solution are initially charged in the same 250 liter reactor and 71 kg (700 mole) of $H_2SiCl_2$ are then metered over a period of 40 minutes at 120°–130° C. Slow addition of 3 liter of cyclopentanone and stirring further at this temperature results in completion of the 1st stage after 2 hours and the gauge pressure has dropped to 2 bar.

For the 2nd stage, 48 kg of cyclopentene containing 2% of cyclopentanone as activator are then metered over a period of 1 hour and the mixture is stirred for an additional 2 hours at 130°–140° C. During this time, the internal pressure falls back continuously to about 2 bar/130° C. The cooled mixture, which is at atmospheric pressure, is subsequently discharged. This gives 179 kg of product containing 79.3% of dicyclopentyldichlorosilane according to GC (in addition 3.5% of cyclopentene and 0.8% of $CpSiHCl_2$, 2.9% of $Cp_2SiHCl$ 15.2% of $CpSiCl_3$ and 4.2% of $SiCl_4$).

Example 7

Comparative experiment without metered addition a) Without addition of activators (not according to the present invention)

If pure dichlorosilane and the respective olefins are mixed in the weight ratios given above in the Examples 1 to 6, i.e., in a molar ratio of about 1:2, together with the platinum catalyst, in a low-pressure reactor (safety valve from 20 bar, see Example 5), very little reaction is observed at first. However, on slow heating the reaction starts above about 60° C., usually very vigorously, and internal temperatures to above 180° C. can quickly be reached in the case of moderate heat removal or in the case of relatively large batches owing to the high molar enthalpy. This corresponds to a vapor pressure of the starting materials, which are still mostly present at this point, of about 20 bar. As a result, in the case of mixtures which are present in bulk form, there is always a risk of a runaway reaction of the batch until aggressive toxic substances are liberated. This has also been observed in a number of laboratory experiments, particularly in the hydrosilylation of isobutene and norbornene. A runaway reaction leads to undesired secondary reactions such as, for example, the polymerization of the olefin, but at least to damage to the catalyst system.

If, in a specific case, the total amounts of cyclopentene +$H_2SiCl_2$ reacted in Example 6 (or Example 5) are heated together with the catalyst in the 250 liter stirred reactor, a exothermic commencement of the 1st stage is observed from 60°–80° C., with pressure peaks to above 20 bar (=hot spots >180° C.). While the liquid temperature returns relatively quickly to the oil thermostat temperature of 130° C., the reactor gauge pressure falls exponentially over a period of 2 hours to 11 bar and even after a stirring time of more than 8 hours remains virtually constant at this temperature. GC analysis then does show 37.8% of $CpSiHCl_2$ and 2.9% of $Cp_2SiHCl$, but also 4.8% of $H_2SiCl_2$, 3.9% of $HSiCl_3$, 41.7% of cyclopentene and, in particular, 5.4% of cyclopentyldihydrogensilane $CpSiH_2Cl$. The concentration of this dihydrogensilane which is mainly responsible for catalyst inhibition barely decreases in the closed reactor, i.e., without activation or removal of volatile constituents, even after a substantially longer stirring time. In a very similar experiment, adding the same amount of Pt catalyst concentrate again also gave only little improvement.

b) Addition of activators (according to the present invention)

Addition of the activators can eliminate any inhibition in less than 2 hours and reactivate the catalyst for the 2nd stage.

Shortly after addition of 5 kg of acetone to the above mixture which has been stirred for 24 hours at 130° C. a very exothermic reaction commences, resulting in heating of the mixture to over 160° C. (pressure peaks up to >20 bar) in about 30 minutes. A steep drop in the internal pressure is then observed, the pressure having fallen exponentially to <6 bar/130° C. after 2 hours. A further 1 kg of acetone is added and the mixture is stirred for an additional 3 hours until the gauge pressure has dropped to about 2 bar/130° C. According to GC, the dark colored crude product then contains 74.5% of $Cp_2SiCl_2$ and 2.6% of $Cp_2SiHCl$, 5.6% of $CpSiCl_3$, 3.7% of $SiCl_4$ and still 4.8% of cyclopentene.

This heating-up experiment shows the (re)activating effect after addition of acetone. At the same time, the significantly lower process control and the resulting lower selectivity of the reaction compared with the corresponding metering-controlled examples, e.g., 1 or 5 and 6, can also be seen.

Example 8

Reaction of cyclohexene with dichlorosilane

As in Example 2, 3.4 mole (280 g) of cyclohexene are first charged in the 1 liter stirred reactor and admixed with 12 g of platinic acid/isopropanol concentrate. The metering in of a total of 255 g (2.5 mole) of dichlorosilane is then commenced at room temperature. After the rapid addition of about 30 g to the stirred initial charge, the mixture is heated to 130° C. and the remaining $H_2SiCl_2$ is metered in over a period of 40 minutes at 130°–140° C. Stirring is continued for an hour at this temperature until the gauge pressure has fallen to below 5 bar or the 1st stage has largely proceeded to completion.

5 g of cyclohexene oxide are carefully metered in over a period of 30 minutes at 120° C. and the mixture is then gently heated. After brief stirring at 120°–140° C., the activation is complete and the 2nd addition stage has just started (pressure drop). A further 199 g (2.4 mole) of cyclohexene are then metered into the reactivated initial charge over a period of about 1 hour at 130°–140° C. and stirring is continued for another 3 hours at this temperature until the pressure ceases to drop.

The addition of 2 g of acetone to the 2nd metered addition significantly accelerates the reaction, by more than half the reaction time.

736 g of crude product containing 79.6% of dicyclohexyldichlorosilane is taken off via the bottom valve. According to GC, the crude product additionally contains 3.3% of dicyclohexylmonochlorosilane, 2.8% of cyclohexyltrichlorosilane, 1.9% of cyclohexane and 8.2% of excess cyclohexene as major secondary constituents.

Reactions of isobutene with dichlorosilane

Example 9

The 1 liter stirred laboratory autoclave is first charged with 314 g (3 mole) of dichlorosilane and 5 g of platinic acid solution. Beginning at room temperature, only 209 g (3.7 mole) of isobutene are then metered into the stirred initial charge via an immersed tube over a period of 40 minutes. After the 1st quarter thereof has been added relatively quickly, the mixture is heated and the remainder is metered sufficiently slowly for the internal temperature to remain at 70°–80° C. and the pressure to remain below 9 bar. After stirring for an additional 20 minutes at up to 90° C., 9 g of tert-butylchloride are added and the mixture is slowly heated to 115° C. Within 2 hours at this temperature, the monoaddition is complete and the dihydrogen intermediate formed as by-product has been removed. GC analysis shows 75.6% of isobutyldichlorosilane and 6.7% of isobutyltrichlorosilane, 2.1% of diisobutyldichlorosilane, 2.7% of diisobutylmonochlorosilane, 3.9% of $SiCl_4$ and some low-boiling by-products.

The 2nd stage is then controlled at 110°–120° C. by metering in an additional 170 g of isobutene over a period of 1 hour. After addition of another 4 g of tert-butyl chloride, the mixture is stirred for about 2 hours at 120°–140° C. The cooled mixture still has a low residual pressure which is condensed in a cold trap (−20° C.) and disposed of. The crude product taken off (665 g) contains, according to GC, 75.6% of diisobutyldichlorosilane, as well as 7.3% of isobutyltrichlorosilane, 2.8% of diisobutylmonochlorosilane, 3.8% of $SiCl_4$ and some more minor by-products having lower retention times.

Example 10

Metering in of isobutene together with $H_2SiCl_2$

First, a mixture of dichlorosilane and isobutene in a molar ratio of 1:1.2 is prepared by first condensing 238 g (4.2 mole) of isobutene into the cooled, stirrable reservoir, then adding 354 g (3.5 mole) of $H_2SiCl_2$ and setting a prepressure of about 15 bar using pure nitrogen. The 1 liter stirred laboratory autoclave is charged with 4 g of isopropanol/platinum solution together with 40 g of toluene and 3 g of tert-butyl chloride while stirring. The addition of the prepared isobutene/$H_2SiCl_2$ mixture is commenced at room temperature, the prepared mixture being metered in a liquid from the stirred reservoir via an immersed tube and a hose connection of stainless steel. After about 50 g of mixture have been added, the catalyst-containing initial charge is heated. A further 450 g (a total of about 3 mole of silane) are then metered over a period of 1 hour in such a way that the reaction temperature remains between 80° and 90° C. 30 minutes later, 6 g of tert-butyl chloride are added and the reaction mixture is carefully heated over a period of 2 hours to 130° C. GC analysis at this point shows 75.4% of isobutyldichlorosilane in addition to 3.2% of isobutyltrichlorosilane, 2.6% of diisobutylmonochlorosilane, 7.4% of toluene and 1.3% of diisobutyldichlorosilane. [By means of decompression of the cooled mixture, it is possible to divert >80% pure isobutyldichlorosilane which is well suited for a 2nd addition to other hydrosilylable olefins.]

The 2nd stage is, as in Example 9, controlled at 120°–130° C. by addition of 175 g of isobutene activated with 2% of tert-butyl chloride over a period of 1 hour. After stirring for an additional 2 hours at this temperature, the reaction is largely concluded. This gives 693 g of crude product solution containing, according to GC, 76.3% of diisobutyldichlorosilane. The crude product additionally contains 3.9% of isobutyltrichlorosilane, 2.3% of diisobutylmonochlorosilane, 5.8% of toluene, 2.7% of $SiC_4$ and some unimportant by-products.

II. Stirred atmospheric-pressure reactor

Example 11

Reaction of cyclopentyldichlorosilane with cyclopentene

A 1 liter three-neck flask provided with a magnetic stirrer is charged with 403 g of about 84% pure cyclopentyldichlorosilane (monostage from Example 2), the contents are heated while stirring to 90° C. and admixed with 3 g of platinic acid solution. A total of 149 g of cyclopentene activated with 3% of acetone are then carefully added dropwise over a period of 2 hours for 90°–100° C. to be able to be maintained in the well-mixed initial charge. After stirring for an additional hour at this temperature, the reflux has largely subsided and the 2nd stage is complete. The GC of the 548 g of crude product taken off shows 89.3% of $Cp_2SiCl_2$ as well as 2.4% of $Cp_2SiHCl$, 1.2% of $CpSiCl_3$ and 3.6% of cyclopentene as main constituents.

Example 12

Addition of ethyldichlorosilane to cyclohexene

A 1 liter three-neck flask is charged with 25 g of cyclohexene, 5 g of acetylacetone and 4 g of isopropanol/Pt solution while stirring. Commencing at room temperature, a total of 528 g of an equimolar mixture of cyclohexene and ethyldichlorosilane (each 2.5 mole) are then added dropwise over a period of 90 minutes to the well-mixed catalyst solution. The first 50 g are added relatively quickly and the remainder only after the initial charge has reached 82° C. After addition of an additional 3 g of acetylacetone, the mixture is stirred for 1 hour until a liquid-phase temperature of over 100° C. has been reached. GC analysis at this point shows 88.6% of cyclohexylethyldichlorosilane as well as 2.9% of ethyltrichlorosilane, 1.3% of cyclohexane and 3.7% of remaining cyclohexene as significant constituents.

III. Continuous hydrosilylation/tube reactor

For the addition of dichlorosilane to the respective desired olefins, a continuous process procedure enables, particularly on a large scale, maximum safety and at the same time a very economical reaction to be achieved. Tube or tube-bundle or even loop reactors make possible very good heat transfer and, if desired, short-term stopping of the process by cessation of metering.

The process was developed in the laboratory on a tube reactor which consists essentially of a winding of a stainless steel tube having a length of about 23 m and an internal diameter of 4 mm (reactor volume 290 ml), which tube was thermostated to the respective temperature in an oil bath. At the end of the tube, the reacted reaction solution is, shortly after the oil bath, conveyed via a discharge or pressure-retention valve set to 20 bar and a cooling section into a 3 liter steel tank which is connected via a safety valve to a scrubber (cooling water). The addition of the starting components was effected by means of metering pumps which conveyed these components as liquids via immersed tubes from corresponding steel reservoirs. For this purpose, dichlorosilane has to be stored in a pressure vessel (fitted with pressure gauge) which is maintained under a $N_2$ prepressure of about 6–15 bar. To avoid unequal metered amounts, in the laboratory experiments dichlorosilane was mixed beforehand with the olefin in the desired ratio and pumped as solution into the reactor using the corresponding prepressure.

In the following examples, 25% to 40% strength solutions of dichlorosilane in cyclopentene were used. For this purpose, a cleaned 3 liter pressure vessel provided with a magnetic stirrer and made inert using $N_2$ is first charged with 1200 g of cyclopentene and then up to 800 g of $H_2SiCl_2$ is conducted from the reservoir into this initial charge. An $N_2$ pressure of up to about 7 bar is then applied.

Example 13

Monoaddition of cyclopentene in 20 min/80° or 130° C.

a) 700 g/h of a 25% strength solution of $H_2SiCl_2$ in cyclopentene are first metered into the above-described tube reactor thermostated to 130° C. At the same time, 29 g/h of a catalyst solution comprising 1 part of isopropanol/Pt concentrate and 3 parts of cyclopentyl chloride (Pt concentration of the solution is 0.5%) are metered via a fine metering pump. This results in a mean residence time of 20 min at 130° C. After over 600 g of reaction mixture have been metered through the tube, a 1st intermediate sample is taken just upstream of the receiver via a diversion tap. GC analysis shows that all the $H_2SiCl_2$ has reacted after only 20 minutes at 130° C. 29.1% of cyclopentyldichlorosilane are found, as well as only 1.1% of $CpSiH_2Cl$, 1.8% of $CpSiCl_3$, 0.4% of $Cp_2SiHCl$ and 57% of excess cyclopentene and some more minor by-products having relatively short retention times.

b) If the same material streams are conveyed through the tube of coil heated to 80° C., i.e., 20 min. residence time at 80° C., also a quantitative conversion of the $H_2SiCl_2$ is found. According to GC, the product now contains 28.6% of monocyclopentyl-dichlorosilane and only 0.5% of dihydrogenalkylsilane $CpSiH_2Cl$, 1.6% of $CpSiCl_3$, and 0.5% of $Cp_2SiHCl$, as well as the usual low boilers.

Example 14

Cyclopentyldichlorosilane in 15 min/140° C.

Using a method similar to Example 13, 980 g/h of a 33% strength solution of dichlorosilane in cyclopentene and 39 g/h of a platinum solution comprising 1 part of concentrate and 2 parts of cyclopentyl chloride (Pt content of 0.66%) are pumped into the tube reactor heated to 140° C. After about 500 g of crude product have been collected in the connected 3 liter pressure vessel, an intermediate sample is again taken upstream of this container. GC analysis shows that $H_2SiCl_2$ is completely reacted after a residence time of only about 15 min. at 140° C. According to GC, the intermediate product obtained contains 38.4% of $CpSiHCl_2$, as well as 1.2% of $CpSiH_2Cl$, 2.3% of $CpSiCl_3$, 2.4% of cyclopentyl chloride and 47.6% of cyclopentene as main constituents.

Example 15

Dicyclopentyldichlorosilane in the tube reactor

The catalyst is reactivated by addition of 2% of t-butyl chloride to the crude monostage from Example 14, collected in the receiver. This mixture is immediately subsequently again fed into the tube reactor heated to 145° C. After a mean residence time of only about 45 min. in the oil bath (metering rate of 342 g/h), more than 80% of the monocyclopentyldichlorosilane has reacted. An intermediate sample now contains, according to GC, 58.3% of Cp$_2$SiCl$_2$ and 1.3% of Cp$_2$SiHCl in addition to 3.7% of CpSiCl$_3$ and 8.6% of remaining CpSiHCl$_2$ and 26% of cyclopentene. This remaining monostage is gradually converted into the dicyclopentyl stage during further stirring of the reaction mixtures from the second pass in the 3 liter receiver. Addition of 2% of acetone, preferably in a separate stirred vessel fitted with N$_2$ bypass, accelerates this post-reaction to completion in 1 to 2 hours.

The addition of 2% of t-butyl chloride as reactivator can also be carried out directly in the 2nd feed into the tube reactor. In this case, residence times of about 1 hour at 145° to 150° C. are required to obtain the same result as in the procedure described.

Example 16

From the tube reactor directly into the standard stirred vessel/2nd stage

A total of 1200 g of the product mixture containing about 29% of monoaddition product obtained at 80° C. in accordance with Example 13b are metered at this rate directly into a 2 liter stirred glass vessel fitted with reflux condenser and N$_2$ bypass which has been charged with 4 g of platinic acid concentrate (=80 mg of Pt) diluted with 30 g of cyclopentanone at an initial 60° C. The flask temperature is regulated in such a way that a moderate cyclopentene reflux is always maintained and the continuously evolved heat of addition can readily be removed by water cooling. The mixture is stirred well for an additional 2 hours while heating, until the internal temperature no longer rises. GC analysis at this point shows 38.7% of Cp$_2$SiCl$_2$ and 1.6% of Cp$_2$SiHCl in addition to 4.1% of CpSiCl$_3$ and 3.8% of CpSiHCl$_2$ and 44.8% of excess cyclopentene.

What is claimed is:

1. A process for preparing di- and trialkylsilanes of the formula

$$R_aR^1R^2_bSiX_c \qquad (I),$$

which comprises reacting mono- and dialkylsilanes of the formula

$$R^1R^2_bSiH_aX_c \qquad (II),$$

with alkenes A having at least 4 carbon atoms, which alkenes are unsubstituted or substituted by fluorine, chlorine or bromine atoms or cyano groups, in the presence of a transition metal catalyst and a hydrocarbon activator, which hydrocarbon activator has at least one functional group selected from the group consisting of an aldehyde, keto or epoxy group and a halogen atom, wherein the hydrocarbon activator having at least one keto group is selected from the group consisting of, acetone, methylethylketone, diethylketone, methylisopropylketone, methylbutylketone, acetylacetone, ethylbutylketone, cyclopentanone and cyclohexanone, where, in the above formulae (I) and (II), R is a branched or cyclic hydrocarbon radical having at least 4 carbon atoms, which radical is unsubstituted or substituted by fluorine, chlorine or bromine atoms or cyano groups, R$^1$ is an alkyl radical having at least 2 carbon atoms, which radical is unsubstituted or substituted by fluorine, chlorine or bromine atoms or cyano groups, R$^2$ is a hydrocarbon radical having at least 2 carbon atoms, which radical is unsubstituted or substituted by fluorine, chlorine or bromine atoms or cyano groups, X is a fluorine, chlorine or bromine atom or an alkoxy radical having from 1 to 18 carbon atoms, which radical is unsubstituted or substituted by fluorine, chlorine or bromine atoms or cyano groups, a is 1 or 2, b is 0 or 1 and c is 1 or 2 with the proviso that in the above formulae (I) and (II), the sum of a, b and c is 3.

2. The process as claimed in claim 1, wherein the alkenes A are branched or cyclic and have from 4 to 18 carbon atoms.

3. The process as claimed in claim 1, wherein the radical R$^1$ has from 2 to 18 carbon atoms.

4. The process as claimed in claim 1, wherein the radical R$^2$ has from 2 to 18 carbon atoms.

5. The process as claimed in claim 1, wherein the radical X is a chlorine atom or an alkoxy radical having from 1 to 6 carbon atoms, which radical is unsubstituted or substituted by fluorine, chlorine or bromine atoms or cyano groups.

6. The process as claimed in claim 1 wherein the activator has at most 18 carbon atoms.

7. The process as claimed in claim 1, wherein the amount of activator is 0.1% to 10% by weight of the total mixture.

8. A process wherein mono- and dialkylsilanes of formula (II) are prepared by reacting silanes of the formula

$$R^2_bSiH_dX_c \qquad (III),$$

with alkenes B, having at least 2 carbon atoms, which alkenes are unsubstituted or substituted by fluorine, chlorine or bromine or cyano groups, in the presence of a transition metal catalyst, where R$^2$ is a hydrocarbon radical having at least 2 carbon atoms, which radical is unsubstituted or substituted by fluorine, chlorine or bromine atoms or cyano groups, X is a fluorine, chlorine or bromine atom or an alkoxy radical having from 1 to 18 carbon atoms, which radical is unsubstiuted or substituted by fluorine, chlorine or bromine atoms or cyano groups, b is 0 or 1, c is 1 or 2, d is 2 or 3, and reacting in the same reaction vessel the thus formed mono- and dialkylsilanes of formula (II) as claimed in claim 1.

* * * * *